US008988088B2

(12) United States Patent
Humbert et al.

(10) Patent No.: US 8,988,088 B2
(45) Date of Patent: Mar. 24, 2015

(54) LIQUID IMMERSION SENSOR

(75) Inventors: Aurelie Humbert, Brussels (BE);
Matthias Merz, Leuven (BE); Roel Daamen, Herkenbosch (NL); Youri Victorovitch Ponomarev, Leuven (BE)

(73) Assignee: Quotainne Enterprises LLC, Wilmington, DE (US)

( * ) Notice: Subject to any disclaimer, the term of this patent is extended or adjusted under 35 U.S.C. 154(b) by 0 days.

(21) Appl. No.: 13/510,368

(22) PCT Filed: Nov. 29, 2010

(86) PCT No.: PCT/IB2010/055480
§ 371 (c)(1),
(2), (4) Date: May 17, 2012

(87) PCT Pub. No.: WO2011/073837
PCT Pub. Date: Jun. 23, 2011

(65) Prior Publication Data
US 2012/0249168 A1  Oct. 4, 2012

(30) Foreign Application Priority Data
Dec. 15, 2009  (EP) .................................... 09179322

(51) Int. Cl.
*G01N 27/04* (2006.01)

(52) U.S. Cl.
CPC ............ *G01N 27/041* (2013.01); *G01N 27/048* (2013.01)
USPC ............................ 324/691; 324/600; 324/649

(58) Field of Classification Search
CPC ........................ G01N 27/041; G01N 27/048
USPC ............... 324/514, 691, 700, 649, 693; 73/86;
116/200; 340/604, 605, 603
See application file for complete search history.

(56) References Cited

U.S. PATENT DOCUMENTS

| 2,098,744 | A | * | 11/1937 | Fiske ............................. 510/255 |
| 3,259,461 | A | * | 7/1966 | Griffin, Jr. et al. ................ 436/6 |
| 3,578,409 | A |   | 5/1971 | Silverman et al. |
| 3,847,547 | A | * | 11/1974 | Delgendre et al. .............. 436/73 |
| 3,943,557 | A | * | 3/1976 | Frazee et al. ..................... 338/34 |
| 4,057,823 | A |   | 11/1977 | Burkhardt et al. |
| 4,224,565 | A | * | 9/1980 | Sosniak et al. ................. 324/694 |
| 4,531,009 | A | * | 7/1985 | Inoue et al. ..................... 560/65 |
| 4,565,455 | A | * | 1/1986 | Bloore et al. ................. 374/164 |
| 4,684,884 | A | * | 8/1987 | Soderlund .................... 324/71.1 |
| 4,819,581 | A | * | 4/1989 | Lakey, Sr. ..................... 119/231 |

(Continued)

FOREIGN PATENT DOCUMENTS

DE  102006050107 A1 *  1/2008
DE  10 2006 050107 A1  6/2008

(Continued)

OTHER PUBLICATIONS

International Search Report and Written Opinion for appln. No. PCT/IB2010/055480 (Apr. 4, 2011).

*Primary Examiner* — Huy Q Phan
*Assistant Examiner* — James Split
(74) *Attorney, Agent, or Firm* — Michael H. Lyons

(57) ABSTRACT

Disclosed is a liquid immersion sensor comprising a substrate (10) carrying a conductive sensing element (20) and a corrosive agent (30) for corroding the conductive sensing element, said corrosive agent being immobilized in the vicinity of the conductive sensing element and being soluble in said liquid.

16 Claims, 4 Drawing Sheets

(56) References Cited

U.S. PATENT DOCUMENTS

Figure 1:
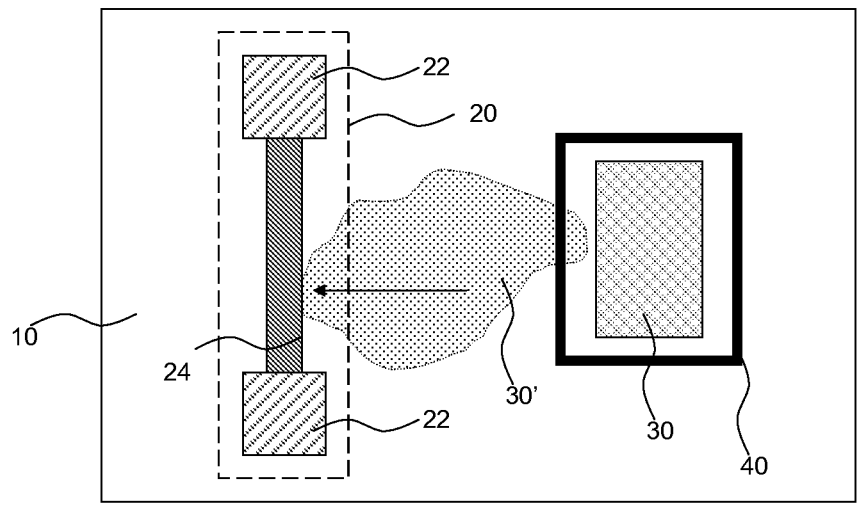

| | | | |
|---|---|---|---|
| 5,606,264 A * | 2/1997 | Licari et al. | 324/755.1 |
| 5,705,018 A * | 1/1998 | Hartley | 156/345.1 |
| 5,939,020 A | 8/1999 | Glaunsinger et al. | |
| 6,024,158 A * | 2/2000 | Gabathuler et al. | 164/61 |
| 6,156,227 A * | 12/2000 | Koefod | 252/70 |
| 6,391,256 B1 * | 5/2002 | Moon et al. | 422/14 |
| 6,603,319 B1 * | 8/2003 | Kasahara et al. | 324/696 |
| 6,894,512 B2 * | 5/2005 | Girshovich et al. | 324/694 |
| 6,997,043 B2 * | 2/2006 | Swanson et al. | 73/49.3 |
| 7,258,005 B2 * | 8/2007 | Nyce | 73/304 C |
| 7,571,637 B2 * | 8/2009 | Chen et al. | 73/73 |
| 7,591,285 B2 * | 9/2009 | Wittmann | 138/104 |
| 2008/0134768 A1 * | 6/2008 | Sanford et al. | 73/73 |
| 2008/0299396 A1 * | 12/2008 | Lin et al. | 428/411.1 |
| 2009/0273480 A1 * | 11/2009 | Mittleman et al. | 340/604 |
| 2010/0182023 A1 * | 7/2010 | Pena et al. | 324/700 |
| 2010/0192688 A1 | 8/2010 | Humbert et al. | |
| 2011/0018097 A1 | 1/2011 | Ponomarev et al. | |
| 2012/0051007 A1 * | 3/2012 | Alvarez et al. | 361/752 |

FOREIGN PATENT DOCUMENTS

| | | |
|---|---|---|
| JP | 2008064561 A * | 3/2008 |
| JP | 2009150806 A * | 7/2009 |
| WO | 2009/016594 A2 | 2/2009 |
| WO | WO 2009115131 A1 * | 9/2009 |

* cited by examiner

LIQUID IMMERSION SENSOR

FIELD OF THE INVENTION

The present invention relates to a liquid immersion sensor comprising a substrate carrying a conductive sensing element.

The present invention further relates to an integrated circuit comprising such a liquid immersion sensor.

The present invention yet further relates to an electronic device comprising such an integrated circuit.

BACKGROUND OF THE INVENTION

Nowadays, integrated circuits (ICs) may comprise moisture sensors, which are included in the ICs to determine whether a malfunctioning IC that has been returned, e.g. to its manufacturer, has been damaged by exposure to moisture, e.g. an immersion event, or whether the IC itself is faulty. The determination of such external influences as a cause of malfunction may be of crucial importance to deciding whether or not the customer returning the IC or an electronic device including the IC is entitled to a warranty claim on the device, as misuse such as the aforementioned immersion event typically invalidates the warranty.

U.S. Pat. No. 4,057,823 discloses a structure for a relative humidity monitor which can be built into an integrated circuit chip. A small area on a silicon chip is made porous by anodic etching. This region is then oxidized and a metal counter electrode is deposited over part of the porous area. Due to the relatively large surface area in the dielectric under the counter electrode and the openness of the structure, ambient moisture can quickly diffuse into the dielectric under the electrode and adsorb onto the silicon dioxide surface, such that changes in ambient humidity will be reflected by measurable changes in capacitance or conductance of the device.

A drawback of such a moisture sensor is that in other to determine if an electronic device returned from the field has been subjected to excess moisture, the sensor must be continuously monitored during the operational life of the electronic device and its measurements, or at least measurements exceeding a predefined threshold, stored for future read-out. This is because the adsorbed moisture may gradually release from the porous area, which means that accurate moisture detection is no longer possible after a prolonged period of time. Continuous monitoring however is an impractical solution, which furthermore cannot be used in passive components.

SUMMARY OF THE INVENTION

The present invention seeks to provide an IC in which its exposure to water does not have to be detected during the actual exposure.

In accordance with a first aspect of the present invention, there is provided a liquid immersion sensor comprising a substrate carrying a conductive sensing element and a corrosive agent for corroding the conductive sensing element, said corrosive agent being immobilized in the vicinity of the conductive sensing element and being soluble in said liquid.

Consequently, the conductive sensing element is exposed to the corrosive agent only when the corrosive agent is immersed in the liquid, e.g. water, which releases the corrosive agent in a dissolved form, which brings the corrosive agent into contact with the conductive sensing element. The corrosion causes permanent damage to the conductive sensing element such that the actual exposure may be detected at a later time, which makes the liquid immersion sensor of the present invention particularly suitable for use in passive components such as RF ID tags which are only activated when placed in a compatible electromagnetic field. Incidentally, the provision of the corrosive agent in an immobilized form prevents the undesirable corrosion of the conductive sensing element in high humidity environments, as the corrosive agent is not (significantly) released under such conditions. Hence, this reduces the risk of false positive readouts, i.e. the false assumption of an immersion event, of such a sensor. It is pointed out that in the context of the present application, the term 'soluble' is intended to include corrosive agents that dissolve in the liquid as well as corrosive agents that are suspended in the liquid.

Preferably, the liquid immersion sensor is integrated in an integrated circuit (IC), wherein the substrate is a semiconductor substrate. This for instance allows the reliable detection of an immersion event for an electronic device comprising such an IC. Such reliable detection is for instance particularly relevant for mobile electronic devices such as mobile communication devices, portable computers, personal digital assistants and so on, where the detection of such an immersion event is relevant to establishing an entitlement to a warranty claim.

In an embodiment, the conductive sensing element comprises a conductive portion extending between opposite contact terminals. This facilitates a straightforward detection of an immersion event simply by measuring an electric parameter of the conductive portion, e.g. resistance or impedance, conductivity, capacitance and so on, as this parameter is typically affected by the corrosion event.

The corrosive agent may be located in wall region to protect the conductive sensing element from exposure to small amounts of the corrosive agent that are released under non-immersion conditions, e.g. during humid conditions in which condensation can occur on the area of the substrate comprising the immobilized corrosive agent. The walls prevent the flow of small amounts of the dissolved corrosive agent to the conductive sensing element.

In an embodiment, the conductive sensing element comprises a plurality of bond pads, each connected to a conductive wire. This allows for a conductive connection of the conductive sensing element to an external terminal, e.g. a connection of the package of an IC. Alternatively, at least some of said conductive wires connect respective bond pads, such that the immersion event may be detected by the corrosion, e.g. destruction, of a wire between such bond pads.

The substrate may comprise a trench extending from the corrosive agent to the conductive sensing element, such that the released corrosive agent may be more effectively guided towards the conductive sensing element.

When integrated into an IC, the IC may further comprise conductive connections to circuit elements, wherein the conductive connections are spatially separated from the corrosive agent such that, upon dissolving the corrosive agent in the liquid, the conductive connections are protected from exposure to the corrosive agent. Such protection may be improved by provision of a barrier structure in between the corrosive agent and the conductive connections.

The integrated circuit may further comprise a measurement circuit conductively coupled to the conductive sensing element for measuring an electrical parameter of the conductive sensing element. In an embodiment, the measurement circuit is adapted to compare the measured electrical parameter with a reference value.

BRIEF DESCRIPTION OF THE EMBODIMENTS

Embodiments of the invention are described in more detail and by way of non-limiting examples with reference to the accompanying drawings, wherein:

FIG. 1-7 schematically depict various embodiments of the liquid immersion sensor of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

In FIG. 1, an embodiment of a liquid immersion sensor in accordance with the present invention is shown. A substrate 10, which may be any suitable substrate, preferably a semiconductor substrate, more preferably a silicon substrate, is provided with a conductive sensing element 20 comprising contact terminals, e.g. bond pads 22 in between which a conductive portion 24 such as a strip or bar of a metal or other conductive material, e.g. poly-Si, susceptible to corrosion is provided.

In the context of the present invention, corrosion is the degradation of metals as a result of electrochemical activity, as will be explained in more detail below.

In an uncorroded state, the electrical parameters of the conductive portion 24 will be indicative of this uncorroded state. Such parameters may therefore be considered reference parameters of the known good state of the conductive portion 24. Any suitable electrical parameter may be measured. For instance, the resistance or impedance of the conductive portion 24 across the terminals 22 may be measured. This may be measured in any suitable manner, e.g. in the voltage or current domain.

The corrosive agent 30 may be immobilized on the substrate 10 in any suitable manner. For instance, the corrosive agent 30 may be adhered to the substrate 10 in a solid or dry form using a liquid-soluble adhesive, e.g. a water-soluble adhesive. Alternatively, the corrosive agent 30 may be placed in a container (not shown) which is either wholly water-soluble or partially water-soluble, e.g. having a water-soluble lid, such that the corrosive agent is released by the (partial) dissolving of its container. Non-limiting examples of suitable water-soluble materials include water-soluble polymers such as PVA (poly vinyl alcohol) polyvinylpyrrolidone, gelatine, hydroxy propyl methyl cellulose, hydroxy methyl ethyl cellulose, hydroxypropyl cellulose and polyethylene oxide. Other suitable materials will be apparent to the skilled person.

In the context of the present invention, the phrase 'immobilized' is intended to mean either fixated onto the substrate or contained on the substrate by a holding structure. In other words, this term is intended to imply that, in normal use, the corrosive agent cannot move freely over the substrate until released by the exposure of the liquid immersion sensor to the liquid of interest, which for most application domains will be water. Nevertheless, it should be understood that the principle of the present invention may be applied to an immersion sensor for any type of liquid.

The general principle of the liquid immersion sensor of the present invention will be explained with the aid of FIG. 1. Upon the immersion of the liquid immersion sensor in a liquid capable of releasing the corrosive agent 30, e.g. by dissolving the corrosive agent 30 and/or its container in case of a corrosive agent 30 immobilized by a container, the corrosive agent 30 will flow in a dissolved form 30' towards the conductive sensing element 20 and the conductive portion 24 in particular.

As previously explained, corrosion is the degradation of metals as a result of electrochemical activity. The process of corrosion requires four components for it to occur:
an anode, i.e. the conductive portion 24;
a cathode, i.e. the corrosive agent 30;
an electrolyte, i.e. the liquid dissolving the cathode
electrical connection between the anode and the cathode, i.e. the electrolyte establishing a physical contact with the anode.

The use of the terms 'anode' and 'cathode' has been purposively chosen as there is a requirement of a potential difference between the two materials; i.e., the anode has a greater tendency to lose electrons while the cathode has a greater tendency to gain them. The presence of this potential difference is the primary driver of corrosion. Hence, in general terms, any combination of anode and cathode materials may be chosen as long as the required potential difference is present and the cathode material is soluble or at least suspendable in the liquid of interest.

Preferably, the conductive portion 24 is selected from the following list of metals in descending order of ability to corrode: Mg, Zn, Al, Cd, Pb, Tin, Ni, Cu, Si, Au and Pt. More preferably, metals are used that are routinely used in semiconductor processing, such as Al, Cu, Ti, Ta, W and alloys thereof, as this means that the liquid immersion sensor may be realized without increasing the complexity of a semiconductor manufacturing process.

Suitable candidates for the corrosion agent 30 may be selected from the group of noble metals, materials having a high oxygen content; and non-metallic components. For instance, the chemical corrosion of Al may be triggered by the presence of contaminants on the die surface. It is for instance known in semiconductor processing that incomplete rinsing or excessive use of corrosive contaminants such as P, S, and Cl during wafer fabrication can make aluminum structures on the semiconductor die highly susceptible to corrosion by these contaminants.

Hence, suitable non-limiting examples of the corrosive agent 30 can include chlorine salts, which in contact with water will create a highly corrosive media. Other contaminants that accelerate corrosion include salts containing bromide, iodide, and cyanide ions. As previously mentioned, corrosive agent 30 may also be a source of $O_2$ that will be dissolved in water, or may be an acidic media. Alternatively, the corrosive agent 30 may be a noble metal, e.g. P or Au to support galvanic corrosion.

Upon the dissolved corrosive agent 30' physically contacting the conductive portion 24, as indicated by the arrow in FIG. 1, the conductive portion 24 corrodes at this contact region. As the corrosion process alters the electrical parameter of the conductive material of the conductive portion 24, e.g. increases its impedance, the exposure of the liquid immersion sensor to a liquid can be simply determined by measuring the electrical parameter of the conductive portion 24 via the connection terminals 22. In case of a (significant) deviation of the measured electrical parameter from its reference value, the (partial) corrosion of the conductive portion 24 has been established, thus indicating that the liquid immersion sensor has been immersed in the liquid, as the established corrosion indicates that the corrosive agent has been released.

Such a measurement may be done in any suitable manner. For instance, in case of a liquid immersion sensor integrated into an IC, the IC may comprise a measurement circuit that is connected to the terminals 22 for measuring the electrical parameter of the conductive portion 24. The IC may contain some form of memory in which the reference value has been stored, with the measurement circuit being adapted to perform a comparison between the measured electrical parameter of the conductive portion 24 and its reference value as previously explained. Alternatively, the terminals 22 may be connected to external terminals of e.g. a package of the liquid immersion sensor, such as a packaged IC containing such a sensor, in which case the measurement may be performed externally via said external terminals.

As an option, the corrosive agent 30 may be surrounded by a wall structure 40, which is provided to prevent or at least reduce the migration of condensation droplets from the region of the corrosive agent 30 to the conductive portion 24. The wall structure 40 preferably is a non-corroding structure. Suitable materials for the wall structure for example include $SiO_2$, SiN, SiC, SiCN, Si and organic polymers.

The surrounding wall 40 typically has a height of no more than a few droplets of the liquid such that droplets formed during condensation in e.g. high humidity conditions cannot easily escape the wall structure 40, while in an immersion event, the volume of the liquid immersing the liquid immersion sensor is typically such that the height of the wall structure 40 can be considered negligible. Consequently, such a wall structure 40 can be advantageously used to largely prevent the corrosion of the conductive portion 24 during non-immersion events causing the release of the corrosive agent 30, such as the aforementioned humid conditions. The height of the wall structure may be chosen in the range from a few hundreds of nanometer to a few microns, e.g. 100-1000 nm. The wall structure 40 may have the same height as the conductive portion 24, as this may simplify the subsequent processing steps of the liquid immersion sensor.

Figure 2:
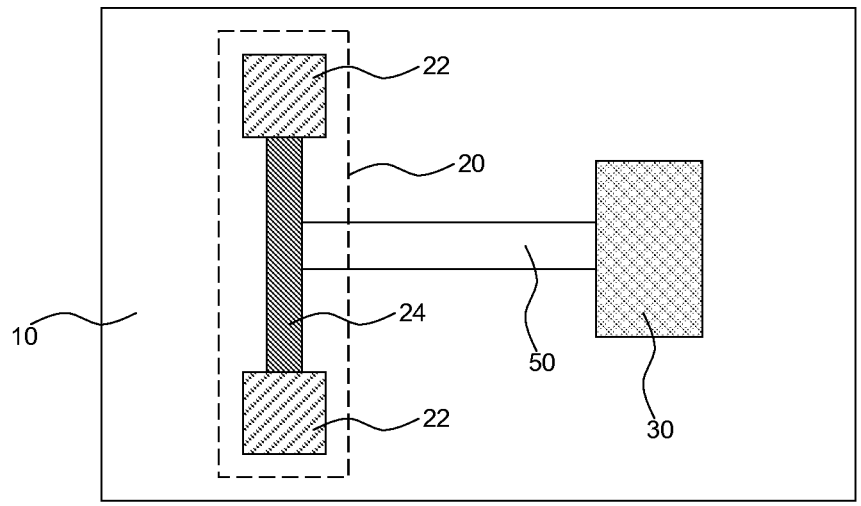
Figure 3:
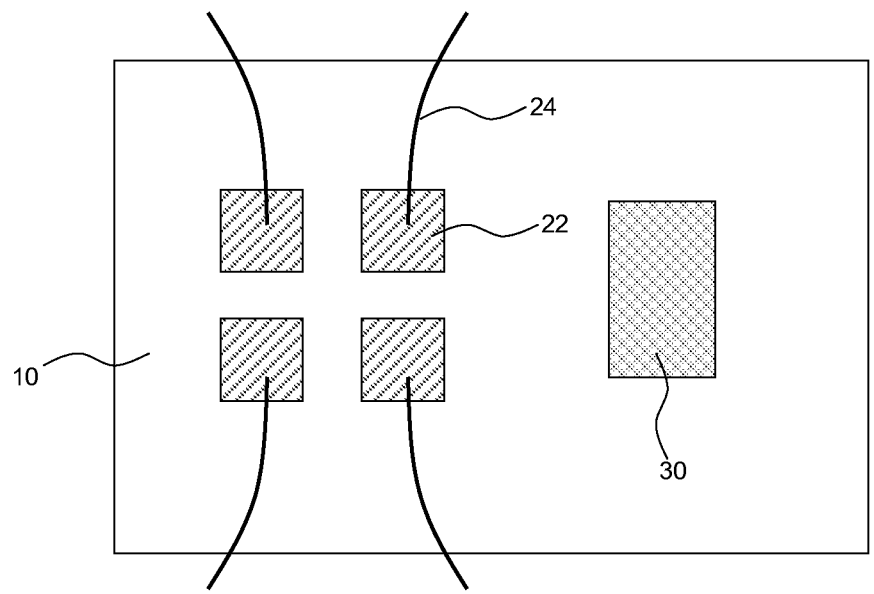

FIG. 2 shows an alternative embodiment of the present invention, in which a trench or channel 50 is formed in the substrate 10 to guide the dissolved corrosive agent 30 from its original location to the conductive portion 24. This has the advantage that the dissolved corrosive agent 30 is more effectively delivered to the conductive portion 24. This not only accelerates the corrosion of the conductive portion 24, but furthermore reduces the risk of the dissolved corrosive agent 30 spilling to unintended parts of the substrate, e.g. other corrosion-sensitive areas that are not designed to be used as corrosion sensing elements.

Figure 4:
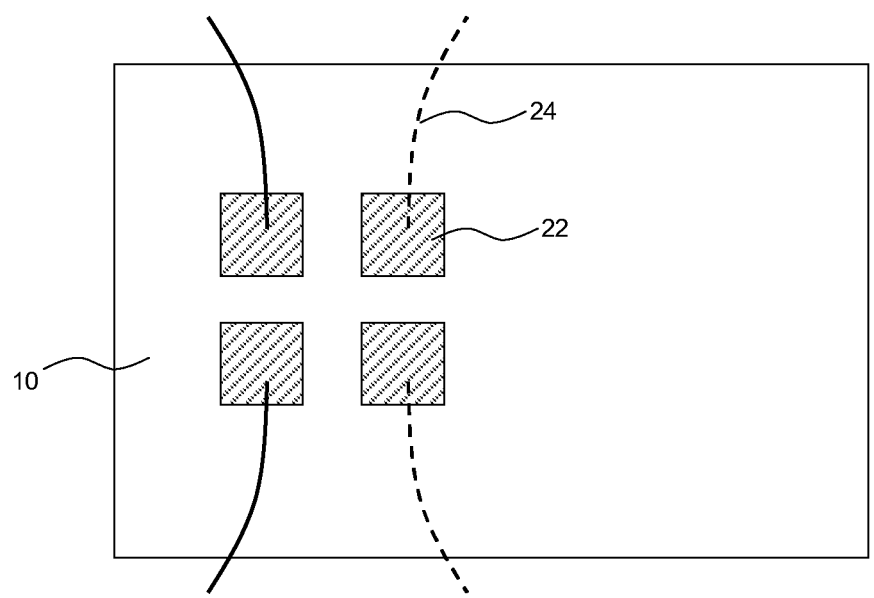

In FIGS. 1 and 2, the conductive portion 24 has taken the shape of a conductive bar mounted on the substrate 10. However, other embodiments of such a conductive portion are equally feasible. For instance, the conductive portion does not require being in physical contact with the substrate 10. In an embodiment shown in FIG. 3, the liquid immersion sensor comprises a plurality of conductive portions 24 in the shape of wires between bond pads 22 and external terminals (not shown) such as the external terminals of an IC package. Upon release of the corrosive agent 30, at least some of the wires 24 are corroded as indicated in FIG. 4 by the dashed lines, such that the electrical parameters of the conductive sensing element 20 formed by the bond pads 22 and the wires 24 is altered. In an embodiment, the thickness of the wires 24 is chosen such that upon exposure of the wires 24 to the dissolved corrosive agent 30, the conductive path of the exposed wires is destroyed, such that the wires effectively operate as a corrosion-sensitive fuse.

Figure 5:
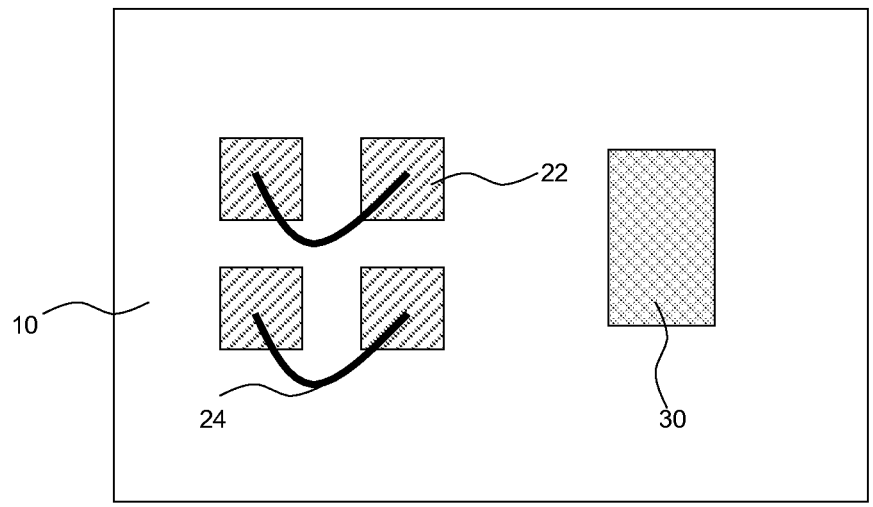

In an alternative embodiment, as shown in FIG. 5, the wires 24 are connected between two bond pads 22 on the substrate 10, with these bond pads conductively connected to further circuitry (not shown) such as the previously described measurement circuit for measuring the electrical parameter(s) of the wires 24 to detect exposure of the wires 24 to the corrosive agent 30.

Figure 6:
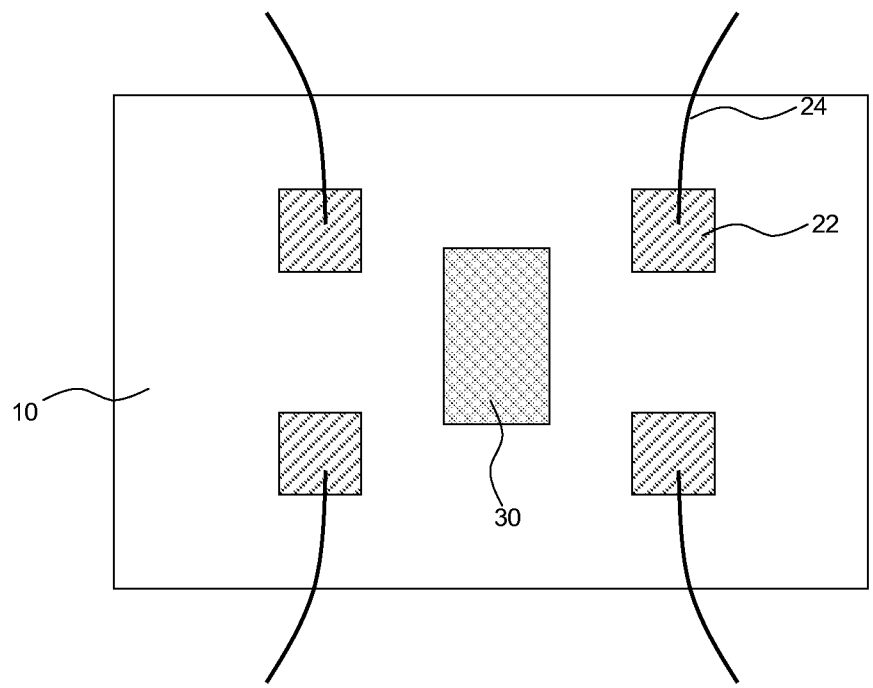
Figure 7:
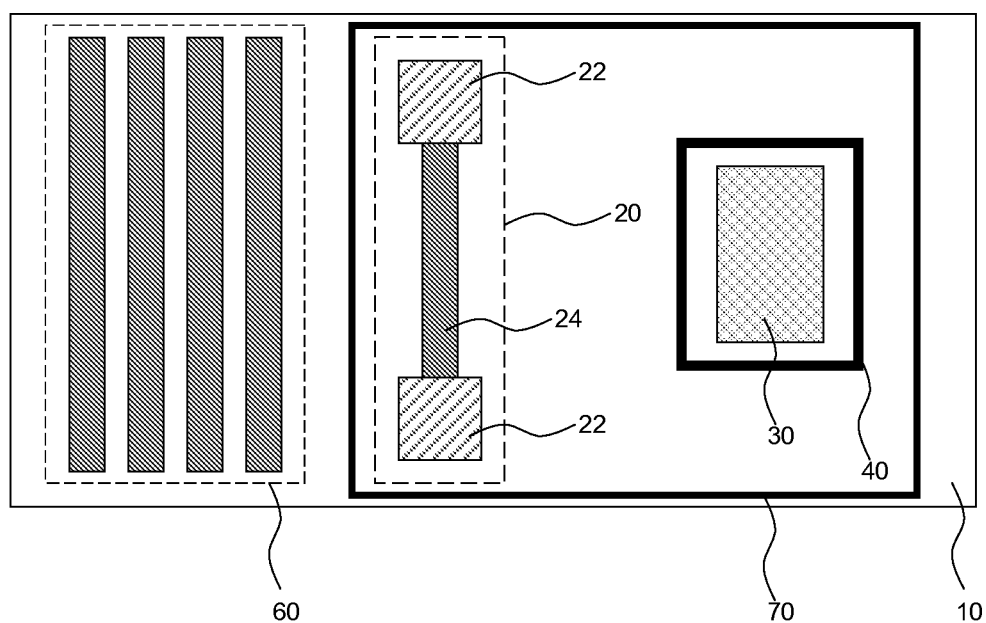

FIG. 6 shows another embodiment of the present invention, in which a plurality of contact terminals 22, e.g. bond pads and conductive portions 24, e.g. wires, are distributed in such a manner that they surround the immobilized corrosive agent 30. This has the advantage at least one of the conductive portions 24 is likely to get corroded because regardless of the direction in which the dissolved corrosive agent will flow following an immersion event, said flow will encounter at least one of the conductive portions 24. Hence, a liquid immersion sensor having improved reliability is thus obtained. The individual contact terminal 22 and conductive portion 24 pairs may form part of separate liquid immersion sensors or may be separate portions of a single liquid immersion sensor.

As previously explained, the liquid immersion sensor may be integrated onto an IC, which will typically comprise further conductive connections such as metallization layers and wires for connecting bond pads to e.g. a lead frame package. In such an embodiment, such further conductive connections preferably should be far enough spaced apart from the corrosive agent 30 such that following an immersion event, corrosive damage to the further conductive connections is avoided or at least limited. In an embodiment, shown in FIG. 7, the conductive sensing element 20 and the immobilized corrosive agent 30 are placed in a separate compartment 70 that acts as a barrier structure between the corrosive agent 30 and the further conductive connections 60 of the IC. Other barrier structures are feasible and will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A liquid immersion sensor for immersion in a liquid comprising:
   a substrate carrying a conductive sensing element and a corrosive agent for corroding the conductive sensing element, said corrosive agent being immobilized and disposed apart from the conductive sensing element and being soluble in said liquid; and
   a wall structure that at least partially surrounds the corrosive agent, wherein the wall structure is disposed between the corrosive agent and the conductive sensing element.

2. The liquid immersion sensor of claim 1, wherein the substrate is a semiconductor substrate.

3. The liquid immersion sensor of claim 1, wherein the conductive sensing element comprises a conductive portion extending between opposite contact terminals.

4. The liquid immersion sensor of claim 1, wherein the conductive sensing element comprises a plurality of bond pads, each said bond pad being connected to a conductive wire.

5. The liquid immersion sensor of claim 4, wherein at least some of said conductive wires connect respective bond pads.

6. The liquid immersion sensor of claim 1 wherein the substrate lies in a plane and wherein the wall structure has a height that extends above the plane of the substrate.

7. The liquid immersion sensor of claim 1 wherein the height of the wall structure and the height of the conductive sensing element are substantially equal.

8. A liquid immersion sensor for immersion in a liquid comprising:
   a substrate carrying a conductive sensing element and a corrosive agent for corroding the conductive sensing element, said corrosive agent being immobilized and disposed apart from the conductive sensing element and being soluble in said liquid, wherein the substrate comprises a trench extending from the corrosive agent to the conductive sensing element.

9. The liquid immersion sensor of claim 8, wherein the corrosive agent is a chloride salt.

10. An integrated circuit comprising the liquid immersion sensor of claim 8.

11. The liquid immersion sensor of claim 8, wherein a liquid-soluble adhesive couples the corrosive agent to the substrate.

12. The liquid immersion sensor of claim 8, wherein the corrosive agent is a bromide salt.

13. The liquid immersion sensor of claim 8, wherein the corrosive agent is an iodide salt.

14. The liquid immersion sensor of claim 8, wherein the corrosive agent is a cyanide salt.

15. The liquid immersion sensor of claim 8, wherein the corrosive agent is an oxygen-generating compound.

16. The liquid immersion sensor of claim 8, wherein the corrosive agent is a noble metal that supports galvanic corrosion.

* * * * *